(12) United States Patent
Casilla et al.

(10) Patent No.: US 10,174,308 B2
(45) Date of Patent: *Jan. 8, 2019

(54) SUCCESSIVE CAPTURE OF NUCLEIC ACID BY MAGNETIC GLASS PARTICLES

(71) Applicant: Roche Molecular Systems, Inc., Pleasanton, CA (US)

(72) Inventors: Alan Casilla, Daly City, CA (US); Jennifer Griswold, Saratoga, CA (US); Cherie Holcomb, Oakland, CA (US); Trevor Hryce, San Francisco, CA (US); Karan Kampani, Oakland, CA (US); Sharon Legaspi, Hayward, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/398,436

(22) Filed: Jan. 4, 2017

(65) Prior Publication Data

US 2017/0191053 A1    Jul. 6, 2017

Related U.S. Application Data

(60) Provisional application No. 62/275,010, filed on Jan. 5, 2016.

(51) Int. Cl.
 C07H 21/00 (2006.01)
 C12N 15/10 (2006.01)
 C12Q 1/6806 (2018.01)

(52) U.S. Cl.
 CPC ....... *C12N 15/1013* (2013.01); *C12Q 1/6806* (2013.01); *C07H 21/00* (2013.01)

(58) Field of Classification Search
 None
 See application file for complete search history.

(56) References Cited

U.S. PATENT DOCUMENTS

| 2003/0012699 | A1* | 1/2003 | Moore | G01N 35/0098 422/400 |
|---|---|---|---|---|
| 2003/0125542 | A1 | 7/2003 | Harttig et al. | |
| 2003/0199078 | A1 | 10/2003 | Kleiber et al. | |
| 2005/0239091 | A1 | 10/2005 | Collis et al. | |
| 2015/0132758 | A1 | 5/2015 | Medina-Llamas et al. | |

FOREIGN PATENT DOCUMENTS

CN    101481400 A    7/2009

OTHER PUBLICATIONS

Berensmeir Appl. Microbiol. Biotechnol. (2006), vol. 73, pp. 495-504.*
Han et al. World J. Microbiol. Biotechnol. (2007), vol. 23, pp. 1041-1045.*
Ainsworth Plant Molecular Biology Reporter (1994), vol. 12, p. 198-203.*

* cited by examiner

*Primary Examiner* — Patrick T Lewis
(74) *Attorney, Agent, or Firm* — Eric Grant Lee

(57) ABSTRACT

Provided herein are methods and components for successive capture of nucleic acids using magnetic glass particles.

17 Claims, 1 Drawing Sheet

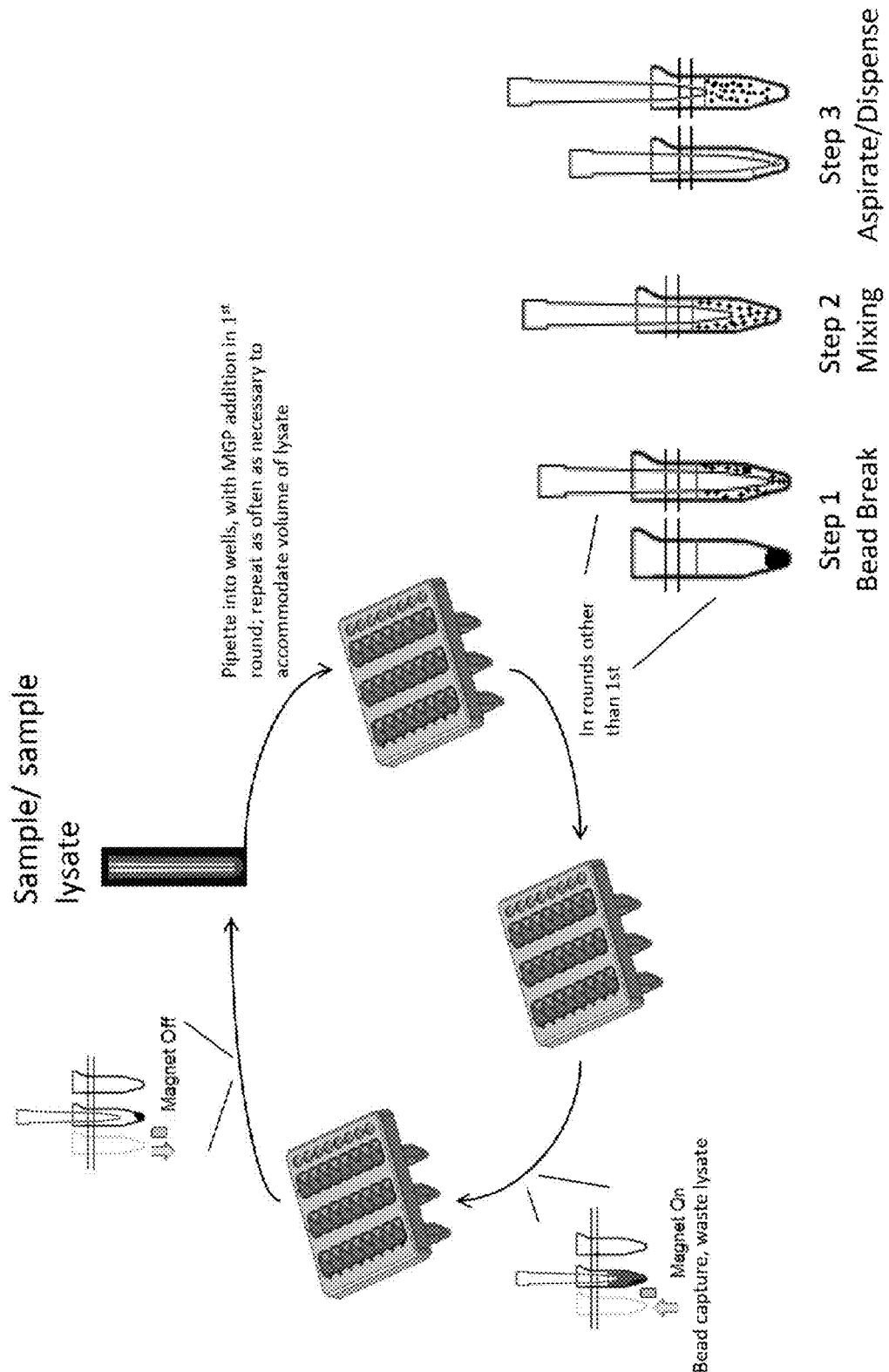

SUCCESSIVE CAPTURE OF NUCLEIC ACID BY MAGNETIC GLASS PARTICLES

BACKGROUND OF THE INVENTION

The concept of "liquid biopsy" has gained traction in recent years. Instead of taking a sample from solid tissue, liquid biopsies capture cells, extracellular vesicles such as exosomes and/or cell-free molecules such as DNA, RNA, or proteins. These components can be collected in biofluids such as blood (or plasma or serum), urine, sputum, and so forth. The presence of these components can be associated with, for example, cancers, tumors, autoimmune diseases, cardiovascular events, viruses, bacterial or pathogenic infection, or related to a drug response. The molecules of interest are often associated with extracellular bodies such as exosomes, or may be "cell-free" in the fluid.

Liquid biopsies can be conducted using any of several biofluids, and can be minimally invasive (e.g., blood collection by phlebotomy) or non-invasive (urine collection). Liquid biopsies are thus attractive for ease of collection, ease of repeat collection for patient monitoring, higher likelihood of patient acquiescence, familiarity of sample collection to patients, and less specialized collection sites.

One drawback of liquid biopsies is that the concentration of nucleic acid can be relatively low, so that a large volume is needed to obtain sufficient material for downstream analysis. Nucleic acid capture kits and devices are typically designed for small sample volumes, typically in the range of 0.2-1 mL.

While magnetic particles are highly useful for nucleic acid capture, ferromagnetic particles become individually magnetized after exposure to a magnetic field. Serial reuse of magnetic particles after an initial magnetic separation step is currently advised against, because it is believed that the particles will be incapable of effectively binding additional nucleic acid. For example, once the particles are individually magnetized, they form a clump that blocks any unoccupied nucleic acid binding sites.

BRIEF SUMMARY OF THE INVENTION

Provided herein are methods and compositions for nucleic acid capture using the same magnetic glass particles (MGPs) for multiple, successive rounds of magnetic capture and purification. These methods are useful for processing large liquid sample volumes in the relatively small vessels used in automated systems.

Provided are methods for capturing nucleic acids in a liquid sample comprising: (a) contacting a first aliquot of the liquid sample with MGPs in a vessel under conditions that allow nucleic acids from the liquid sample to non-covalently bind the MGPs, wherein the MGPs comprise at least one magnetic core in glass, and are ferromagnetic and non-porous; (b) applying a magnetic field to the MGPs; (c) removing unbound liquid sample from the MGPs; (d) contacting a second aliquot of the liquid sample with the MGPs; (e) resuspending the MGPs in the second aliquot of the liquid sample; (f) pipetting the MGPs to mix the MGPs throughout the second aliquot of liquid sample; (g) applying a magnetic field to the MGPs; (h) removing unbound liquid sample from the MGPs; and (i) optionally repeating steps (d)-(h) for at least one additional aliquot of liquid sample (e.g., a third, fourth, fifth, or sixth aliquot). In some embodiments, step (f) comprises pipetting the MGPs to the top of the second (or later) aliquot of liquid sample and dispensing the MGPs. In some embodiments, the method is practiced for three, four, five, or six aliquots of the liquid sample.

In some embodiments, the MGPs have a mean diameter of 0.5-15 um, e.g., 1-10 um, 0.8-2 um. In some embodiments, the glass comprises at least one metal oxide. In some embodiments, the metal oxide is selected from $SiO_2$, $B_2O_3$, $Al_2O_3$, $K_2O$ CaO, and ZnO. In some embodiments, the glass comprises $SiO_2$, $B_2O_3$, $Al_2O_3$, $K_2O$ CaO, and ZnO in order of molar percentage. In some embodiments, the glass comprises $SiO_2$, $B_2O_3$, $Al_2O_3$, $K_2O$, and CaO in order of molar percentage.

In some embodiments, steps (a)-(i) are carried out in the presence of a chaotrope, e.g., guanidinium thiocyanate, guanidine hydrochloride, or urea. In some embodiments, the method further includes eluting nucleic acids from the MGPs, e.g., in a liquid or buffer comprising a lower concentration of chaotrope than present in steps (a)-(i), or substantially lacking chaotrope (e.g., water or buffer). In some embodiments, step (c) comprises removing unbound liquid sample from the MGPs, washing the MGPs, and removing unbound material from the MGPs. In some embodiments, step (h) comprises removing unbound liquid sample from the MGPs, washing the MGPs, and removing unbound material from the MGPs. In some embodiments, steps (c) and (h) comprise removing unbound liquid sample from the MGPs, washing the MGPs, and removing unbound material from the MGPs.

In some embodiments, the liquid sample is blood, plasma, serum, urine, saliva, semen, cerebral spinal fluid, or a lysate thereof. In some embodiments, the liquid sample is plasma or serum. In some embodiments, the liquid sample is urine. In some embodiments, the liquid sample has a volume of at least 2 mL, e.g., 4, 5, 10, 50, 2-10, 4-50, or 2-100 mL.

In some embodiments, the vessel holds (e.g., has a maximum working capacity of) 5 mL or less (e.g., 3, 2, or 1 mL or less). In some embodiments, the vessel holds 0.2-1.5 or 0.5-2 mL. In some embodiments, the vessel is a well in a multi-well plate or cartridge. In some embodiments, the vessel is a tube.

In some embodiments, the method is carried out in an automated device. In some embodiments, steps (b)-(i) are carried out in an automated device. In some embodiments, the method further comprises eluting the nucleic acids from the MGPs, e.g., in the automated device.

In some embodiments, the nucleic acids are RNA. In some embodiments, the nucleic acids are DNA. In some embodiments, the method further comprises reverse transcription (e.g., if the liquid sample includes RNA) and/or PCR (e.g., to amplify DNA in the liquid sample or the reverse transcription cDNA product). In some embodiments, the reverse transcription and/or PCR is carried out in the presence of the MGPs. In some embodiments, the reverse transcription and/or PCR is carried out in the absence of the MGPs, e.g., after elution. In either case, the reverse transcription and/or PCR can be automated either on the same automated device used for separation or on a separate automated device.

BRIEF DESCRIPTION OF THE DRAWINGS

FIG. 1 shows an embodiment of the disclosed method for successive capture of nucleic acids with three rounds of capture of nucleic acids from the same sample following the initial capture round. Initially, sample and magnetic glass particles (MGPs) are mixed (put in contact) in a vessel, a magnet is applied to the vessel to collect the nucleic acid bound MGPs, unbound liquid is aspirated, and the magnet is removed. FIG. 1 shows that additional sample is added for the steps of Bead Break, Mixing, and Aspirate/Dispense. Bead Capture and removal of unbound liquid (Waste Lysate) are carried out as before.

DETAILED DESCRIPTION OF THE INVENTION

I. Introduction

Large-volume liquid samples, e.g., from liquid biopsies, non-invasive prenatal testing, and potentially pathogen (viral, bacterial, fungal) containing fluids, are increasingly used for diagnostic testing. These liquid samples can be large relative to the vessels (e.g., wells or tubes) compatible with automation, and are often dilute, having a low concentration of nucleic acid. The present methods allow for stream-lined and automated nucleic acid or protein capture from large volumes of liquid using one set of magnetic particles. Aliquots of the liquid are exposed to the magnetic particles in successive rounds. With each successive round, more of the bead surface becomes occupied with nucleic acid or protein from the liquid sample. By carrying out successive rounds, sufficient nucleic acid can be gathered for downstream assays such as PCR or sequencing.

The method involves an initial round of exposing magnetic glass particles (MGPs) to the first aliquot of liquid sample, optional mixing, applying a magnetic field to the MGPs to form a clump (pellet), and separating the unbound liquid from the MGP clump. The MGP clump is then exposed to the second aliquot of liquid sample and physically disrupted (e.g., with the pipette tip or by force of liquid pipetting). The disrupted MGPs are then dispersed (e.g., evenly dispersed) throughout the second aliquot, allowing the MGPs to mix and bind to nucleic acids in the sample. Again, a magnetic field is applied to the MGPs to form a clump, and unbound liquid is removed. A third, fourth, fifth, or additional successive rounds can be carried out until sufficient nucleic acid or protein is gathered, or until the entire liquid sample has been exposed to the MGPs.

II. Definitions

The term "magnetic glass particle" or "MGP" refers to a particle comprising glass that non-covalently binds nucleic acids, and at least one magnetic core (e.g., a dispersion of magnetic cores) that respond to a magnetic field. The glass is not necessarily pure silica, though silica can be a component. MGPs are small enough to be pipetted in a standard pipette tip and form a suspension, typically 0.5-15 um. MGPs are roughly spherical on average, and can be porous or non-porous. The magnetic core can be ferromagnetic or paramagnetic (only magnetized in the presence of a magnetic field). Suitable MGPs are described in more detail, e.g., in U.S. Pat. Nos. 6,255,477 and 6,545,143. The terms "pellet," "clump," and like terms refer to the grouping of MGPs formed in the presence of a magnetic field.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

The words "protein," "peptide," and "polypeptide" refer to an amino acid polymer or a set of two or more interacting or bound amino acid polymers. The terms apply to amino acid polymers in which one or more amino acid residue is an artificial chemical mimetic of a corresponding naturally occurring amino acid, as well as to naturally occurring amino acid polymers, those containing modified residues, and non-naturally occurring amino acid polymer.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, e.g., an a carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

The term "antibody" refers to a polypeptide comprising a framework region from an immunoglobulin gene, or fragments thereof, that specifically bind and recognize an antigen, or any desired target. Typically, the "variable region" contains the antigen-binding region of the antibody (or its functional equivalent) and is most critical in specificity and affinity of binding. See Paul, Fundamental Immunology (2003).

Intact antibodies can be described according to isotype, as defined by the heavy chain constant region. Antibody light chains are classified as either kappa or lambda. Heavy chains are classified as gamma, mu, alpha, delta, or epsilon, which in turn define the isotype classes, IgG, IgM, IgA, IgD and IgE, respectively.

Antibodies can exist as intact immunoglobulins or as any of a number of well-characterized fragments that include specific antigen-binding activity. Such fragments can be produced by digestion with various peptidases. Pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region, thereby converting the F(ab)'2 dimer into an Fab' monomer. The Fab' monomer is essentially Fab with part of the hinge region (see Fundamental Immunology (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., Nature 348:552-554 (1990)).

The term "capture," "capturing," "bind," or "binding," in the context of an MGP binding nucleic acid, refers to non-covalent binding, e.g., through chaotropic or ionic interaction. The MGP-nucleic acid interaction can be disrupted by elution, e.g., using an elution buffer that interferes with the non-covalent interaction. The terms can also refer to binding of an MGP to a protein, e.g., via an antibody-antigen, receptor-ligand, or streptavidin-biotin interaction. In such embodiments, a target-binding moiety (e.g., antibody) is bound to the MGP to allow for specific affinity purification of a target in the liquid sample.

The term "primer" refers to a short nucleic acid (typically an oligonucleotide of about 8-40, 6-20, 12-50 or 15-25 nucleotides) that acts as a point of initiation of polynucleotide strand synthesis by a nucleic acid polymerase under suitable conditions. Unless otherwise described, an "extension product" is the polynucleotide strand that extends from the 3' end of the primer upon synthesis. Polynucleotide synthesis and amplification reactions typically include an appropriate buffer, dNTPs and/or rNTPs, and one or more optional cofactors, and are carried out at a suitable temperature. A primer typically includes at least one region that can hybridize a target sequence and that is at least substantially complementary to a target sequence. This region of is typically about 15 to about 40 nucleotides in length, and includes 0, 1, 2, or 3 mismatches.

The term "amplification product" refers to the product of an amplification reaction. The amplification product includes the primers used to initiate each round of polynucleotide synthesis. An "amplicon" is the sequence targeted for amplification, and the term can also be used to refer to amplification product. The 5' and 3' borders of the amplicon are defined by the forward and reverse primers.

The term "sample" or "biological sample" refers to any composition containing or presumed to contain nucleic acid. The term includes purified or separated components of cells, tissues, or blood, e.g., DNA, RNA, proteins, cell-free portions, or cell lysates. In the context of the presently disclosed device, the sample is liquid, e.g., blood or a blood component (plasma or serum), urine, semen, saliva, sputum, mucus, semen, tear, lymph, cerebral spinal fluid, mouth/throat rinse, bronchial alveolar lavage, material washed from a swab, etc. Samples also may include constituents and components of in vitro cultures of cells obtained from an individual, including cell lines. The liquid sample can also be partially processed from a sample directly obtained from an individual, e.g., cell lysate or blood depleted of red blood cells.

In the context of the present disclosure, the term "unbound liquid" or "unbound sample" refers to liquid and other components (e.g., proteinaceous material or cell debris) that is not bound to the MGP, e.g., liquid depleted of nucleic acids or other target. The unbound liquid may still include a residual amount of nucleic acids or target.

Extracellular vesicles, including exosomes, microvesicles, and apoptotic bodies, are cell derived vesicles (membrane enclosed body) present in biological fluids, e.g., blood and urine. Extracellular vesicles can be released from cells, e.g., directly from the plasma membrane, or formed when multivesicular bodies fuse with the plasma membrane. Extracellular vesicles typically include components such as nucleic acids and proteins from their cell of origin. Exosomes are typically 40-120 nm in diameter, microvesicles are typically 50-1000 nm in diameter, and apoptotic bodies are typically 500-2000 nm in diameter.

A "control" sample or value refers to a sample that serves as a reference, usually a known reference, for comparison to a test sample or test conditions. For example, a test sample can be taken from a test condition, e.g., from a sample processed using the presently described methods, and compared to samples from known conditions, e.g., from a sample not processed using the presently described methods, or from a sample having a known amount of nucleic acid. A control can also represent an average value or a range gathered from a number of tests or results. A control can also be prepared for reaction conditions. For example, a positive control for the presence of nucleic acid could include primers or probes that will detect a sequence known to be present in the sample, while a negative control would be free of nucleic acids. One of skill in the art will recognize that controls can be designed for assessment of any number of parameters. Controls can be designed for in vitro applications. One of skill in the art will understand which controls are valuable in a given situation and be able to analyze data based on comparisons to control values. Controls are also valuable for determining the significance of data. For example, if values for a given parameter are widely variant in controls, variation in test samples will not be considered as significant.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989); Ausubel et al.: Current Protocols in Molecular Biology 1987, J. Wiley and Sons, NY; Pfaffl, Methods: The ongoing evolution of qPCR, vol. 50 (2010); van Pelt-Verkuil et al. Principles and Technical Aspects of PCR Amplification, Springer (2010).

III. Methods and Components for Successive Nucleic Acid Capture

A. Biological Sample

The biological sample used in the presently disclosed methods is a liquid including nucleic acids or protein. Sample types include blood (including plasma or serum), urine, saliva, sperm, oral or nasal rinses, cerebral fluid, sputum, cell suspensions (such as blood), lysate from cells or tissues, etc. The sample can be from a single individual (e.g., a patient), or a population of individuals.

The present methods can also be applied to liquids, e.g., prepared from food or plant samples or from wipes of surfaces, e.g., in a hospital setting.

In a sample that includes cells, the cells can be separated out (e.g., using size-based filtration or centrifugation), thereby leaving cell free nucleic acids (cfNA), including nucleic acids in exosomes, microvesicles, viral particles, or those circulating freely. Alternatively, the cells can be lysed to obtain cellular nucleic acids, either in the presence of MGPs or before addition of the cellular lysate to the MGPs.

B. Magnetic Glass Particles

Magnetic glass particles (MGPs) are known in the art, and are described, e.g., in U.S. Pat. Nos. 6,255,477 and 6,545,143. The particles used for the presently described methods are ferromagnetic. The particles are on average roughly spherical with a diameter of 0.5-15 um (e.g., 1-10, 0.8-2, or 1-1.5 um). In some embodiments, the particles are non-porous.

The MGPs can have a single magnetic core coated by glass, or comprise glass infused with several magnetic objects. The magnetic substance can be iron or iron oxide as magnetite ($Fe_3O_4$) or $Fe_2O_3$ (e.g., gamma-$Fe_2O_3$). Barium ferrite, nickel, cobalt, Al—Ni—Fe—Co alloys or other ferromagnetic substances can be used. Metal oxides can also be included in the magnetic core, e.g., aluminum oxide, iron oxide, chromium oxide, copper oxide, manganese oxide, lead oxide, tin oxide, titanium oxide, zinc oxide, or zirconium oxide.

The glass component is typically silica based, e.g., silicon oxide and glass powder, alkylsilica, aluminum silicate, or, NH2-activated silica. In some embodiments, the glass comprises at least one metal oxide (e.g., $SiO_2$, $B_2O_3$, $Al_2O_3$, $K_2O$, CaO, and/or ZnO). In some embodiments, the glass comprises $SiO_2$, $B_2O_3$, $Al_2O_3$, $K_2O$, and CaO, in order of molar percentage. In some embodiments, the glass comprises $SiO_2$, $B_2O_3$, $Al_2O_3$, $K_2O$, CaO, and ZnO, in order of molar percentage. In some embodiments, in addition to $SiO_2$, the glass can include $B_2O_3$ (0-30%), $Al_2O_3$ (0-20%), CaO (0-20%), BaO (0-10%), $K_2O$ (0-20%), $Na_2O$ (0-20%), MgO (0-18%), $Pb_2O_3$ (0-15%), ZnO (0-6%). In some embodimenh:, the glass comprises about 70-75% SiO2, about 14-16% B2O3, about 4-6% Al2O3, about 4-5% K2O, about 2-3% CaO, and about 0-5% ZnO. Appropriate MGPs are commercially available in MagNAPure kits from Roche.

Nucleic acid binds to MGPs in chaotropic solution. Chaotropic solutions can include guanidinium thiocyanate (GuSCN), guanindine hydrochloride, urea, sodium iodite, sodium perchlorate, thiocyanate ion, iodine ion, perchlorate nitrate ion, bromine ion, acetate ion, chlorine ion, fluorine ion, or sulfur ion, or combinations thereof. In some embodiments, the chaotrope is in solution at about 1-10 M, e.g., 2-8 or 4-6 M, to allow nucleic acid binding.

C. Automation

The present methods can be practiced in manual, semi-automated, or automated format. Automation is of course advantageous for reducing time spent handling multiple samples and multi-step processes, contamination between samples and within a sample at different steps of processing, repetitive injuries, and exposure to potentially hazardous substances such as blood samples.

Any instrument capable of carrying out magnetic separation using MGPs can be used. Depending on the device, samples can be processed in multivessel cartridges or plates, or in individual vessels. Vessels (e.g., processing tubes or wells) for use in automated instruments typically hold a liquid volume of 50 uL to 4 mL, more typically 1-2 mL.

Examples of instruments that can be used for automating the presently disclosed methods include but are not limited to the MagNA Pure instruments (Roche), Dynamag® instruments (Thermo Fisher) QIAsymphony® systems (Qiagen), and Maxwell® instruments (Promega).

In some embodiments, the instrument carries out the entire process, e.g., pipetting sample from a large volume in successive aliquots into the processing vessel, carrying out the successive rounds of nucleic acid capture on the MGPs, MGP magnetic collection, removal of unbound liquid, resuspension of the MGPs in the next sample aliquot, and elution of the nucleic acids from the MGPs. In some embodiments, the instrument carries out the successive rounds of nucleic acid capture on the MGPs, MGP sedimentation, removal of unbound liquid, and resuspension of the MGPs in the next sample aliquot. In some embodiments, the same large liquid sample is accessed multiple times for successive rounds. In some embodiments, the user or the instrument "prealiquots" the larger liquid sample into multiple aliquots that are successively accessed for capture, etc.

D. Further Processing and Detection

Further purification of nucleic acids from the clarified sample can be accomplished according to standard methods, e.g., as described in Sambrook, supra. Nucleic acids present in liquid biopsies are often short, e.g., 50-5000 nucleotides in length. The selected purification method should take this into account. Traditional methods include organic extraction, ethanol precipitation, and resuspension; and separation on glass or magnetic beads followed by elution. Kits for DNA and RNA are also commercially available, e.g., High Pure kits from Roche and Wizard kits from Promega.

Nucleic acids are typically eluted from the beads before analysis, though MGPs are compatible with some assays (e.g., detection of a labeled probe hybridized to nucleic acid on the MGP, PCR, or where elution occurs as part of the assay, such as Southern blotting). Elution conditions interfere with the non-covalent (e.g., chaotropic or ionic) interaction of nucleic acid with the MGP, e.g., water, buffer with lower chaotrope concentration than used for binding nucleic acids to the MGPs, and/or elevated temperature, as will be appreciated by one of skill in the art.

The purified nucleic acid sample can be used for detection, e.g., using next generation sequencing, microarray (RNA or DNA), Southern or Northern Blot, or nucleic acid amplification, e.g., using any primer-dependent method. DNA-based methods can be used for amplification and detection, e.g., PCR. In some embodiments, real time or quantitative PCR is used (RTPCR or qPCR). qPCR allows for reliable detection and measurement of products generated during each cycle of PCR process. Such techniques are well known in the art, and kits and reagents are commercially available, e.g., from Roche Molecular Systems, Life Technologies, Bio-Rad, etc. See, e.g., Pfaffl (2010) *Methods: The ongoing evolution of qPCR* vol. 50. In some embodiments, the probe portion of the branched primer-probe is dual labeled (e.g., a TaqMan, CPT, LNA, or MGB probe) with a quencher and a fluorophore (see, e.g., Gasparic et al. (2010) *Anal. Bioanal. Client.* 396:2023).

In some embodiments, a preliminary reverse transcription step is carried out (also referred to as RT-PCR, not to be confused with real time PCR). See, e.g., Hierro et al. (2006) 72:7148. The term "qRT-PCR" as used herein refers to reverse transcription followed by quantitative PCR. Both reactions can be carried out in a single tube without interruption, e.g., to add reagents. For example, a polyT primer can be used to reverse transcribe all mRNAs in a sample with a polyA tail, or a primer can be designed that is specific for a particular target transcript that will be reverse transcribed into cDNA. The cDNA can form the initial template strand to be used with the presently described branched primer-probe, or the other member(s) of its primer pair or primer set. Additional RNA-based methods of amplification can also be used, e.g., nucleic acid sequence based amplification (NASBA) or transcription mediated amplification (TMA).

Detection devices are known in the art and can be selected as appropriate for the selected labels. Detection devices appropriate for quantitative PCR include the Cobas® and Light Cycler® systems (Roche), PRISM 7000 and 7300 real-time PCR systems (Applied Biosystems), etc.

Proteins can be eluted by interfering with their interaction with the target-binding moiety attached to the bead. Elevated temperature can be used, or by varying pH or salt concentration. For streptavidin-biotin interactions, a formamide solution can be used.

Proteins are typically detected using immunoassays or activity assays. Immunoassays include various types of ELISA, Western blots, FACS, or other detection using a labeled antibody (see, e.g., Rich, *The Immunoassay Handbook* (Elsevier $4^{th}$ ed. 2013)). One of skill will understand how to detect the appropriate activity assay depending on the targeted protein, e.g., phosphorylation activity of a kinase target.

IV. Examples

A method to purify nucleic acids from large volumes of liquid (e.g., 4 mL or more) is provided in a typical automated platform that can accommodate a sample volume in the range of 0.5-2 mL. The approach is to use successive rounds of capture of the nucleic acids on the MGPs as shown in FIG. 1.

Example 1

Known amounts of purified cell line DNA and linearized plasmid were spiked into PBS and percent recovery (yield) was measured by qPCR. Four (4) mL sample was lysed off-board with 4.5 mL MagNAPure 96 Lysis Buffer (Roche) and Proteinase K in an appropriately sized tube. The lysate was vortexed to mix and then added onto the instrument deck of either the Instrument 1 or Instrument 2. An aliquot of the lysed sample was added to the process well for automated nucleic acid capture on MGPs. MGPs were added in the initial step and mixed with sample by pipetting. The MGPs were captured using a magnet applied to the side of the process well, and liquid lysate was aspirated, leaving only nucleic acid-bound MGPs in the processing well. The next aliquot of the same sample was added to the same process well and mixed with the MGPs. The mixing involved breaking the clump of magnetized MGPs by pipetting at the bottom of the well. At this point, the beads were suspended in the bottom half of the liquid volume. The bead suspension was pipetted from the bottom of the processing well and dispensed at the top, allowing the MGPs to trickle through the liquid. This process was repeated to ensure that the MGPs were thoroughly exposed to nucleic adds in the second aliquot. The MGP capture and aspiration steps were repeated as in the first round, and the next aliquot of the sample was added to the same processing well, mixed with the MGPs, etc. The entire sample volume of 83 mL was processed in the same processing well using the same MGPs.

Use of the binding/bead capture using baseline Protocol 1 (lacking bead break, but including some aspiration and dispensing) showed that genomic DNA and linearized plasmid were captured with reasonable efficiency on Instrument 1 (78.6% and 79.8%, respectively), comparable to binding/bead capture on Instrument 2 (81.7% and 85.2%, respectively).

The results were compared using the modified method described above (Protocol 2) as shown in FIG. 1. Protocol 2, which includes mechanical resuspension and mixing of the magnetized MGPs, resulted in a 10.7% increase in recovery for beta globin and 22.2% increase in recovery for pEF056. All successive rounds used this modified Protocol 2. Results are shown in Table 1.

TABLE 1

Binding of nucleic acids and successive rounds of bead capture can be executed with excellent resultant yields of DNA

| | Purification Protocol | | | | | | | | |
|---|---|---|---|---|---|---|---|---|---|
| | Instrument 1 Protocol 1 | | | Instrument 2 Protocol 1 | | | Instrument 2 Protocol 2 | | |
| PCR Target | Ave. Cp** | SD | % Yield | Ave. Cp** | SD | % Yield | Ave. Cp** | SD | % Yield |
| pEF056 | 28.6 | 0.0 | 85.2% | 28.7 | 0.0 | 79.8% | 28.4 | 0.1 | 102.0% |
| beta-globin | 30.5 | 0.1 | 81.7% | 30.6 | 0.1 | 78.6% | 30.4 | 0.0 | 89.3% |

**Average of two purifications

Example 2

The bead-breaking method was repeated as shown in FIG. 1. In this example, known amounts of target DNA fragments were spiked into blood, and percent recovery (yield) was measured by qPCR. Eight (8) mL of plasma was used, requiring 4 aliquots to be applied to the beads, which were reused throughout all 4 rounds of nucleic acid binding. In addition, the elution temperature used to remove nucleic acids from the beads after the successive rounds of binding was greatly reduced. This, potentially combined with the small fragment lengths used as targets, resulted in lower yields compared to those shown in Table 1.

If the beads were not effective at binding the target nucleic acids in successive rounds, the maximum yield that could be expected is 25%, only the first of 4 rounds would yield target nucleic acid. However, as shown in Table 2, significant target nucleic acid was bound in successive rounds and recovered for qPCR.

TABLE 2

| PCR Target | Percent Yield | CV (%) |
|---|---|---|
| 66 bp | 49.5% | 3.4 |
| 86 bp | 66.1% | 1.1 |
| 150 bp | 48.3 | 1.6 |

While the foregoing invention has been described in smile detail for purposes of clarity and understanding, it will be clear to one skilled in the art from a reading of this disclosure that various changes in form and detail can be made without departing from the true scope of the invention. For example, all the compositions and techniques and described above can be used in various combinations. All publications, patents, patent applications, websites, and database entries cited in this application are incorporated by reference in their entireties for all purposes.

What is claimed:

1. A method for capturing nucleic acids in a liquid sample comprising:
   (a) contacting a first aliquot of the liquid sample with magnetic glass particles (MGPs) in a vessel under conditions that allow nucleic acids from the liquid sample to non-covalently bind to MGPs, wherein the MGPs are non-porous and comprise at least one ferromagnetic magnetic core in glass;
   (b) applying a magnetic field to the MGPs;
   (c) removing unbound liquid sample from the MGPs;
   (d) contacting a second aliquot of the liquid sample with the MGPs;

(e) resuspending the MGPs in the second aliquot of the liquid sample;

(f) pipetting the MGPs to the top of the second aliquot and dispensing the MGPs;

(g) applying a magnetic field to the MGPs to form a clump of MGPs;

(h) removing unbound liquid sample from the clump of MGPs; and (i) optionally repeating steps (d) through (h) for at least one additional aliquot of liquid sample.

2. The method of claim 1, wherein the MGPs have a mean diameter between 0.5-15 μm.

3. The method of claim 1, wherein the glass comprises at least one metal oxide.

4. The method of claim 3, wherein the at least one metal oxide is selected from $SiO_2$, $B_2O_3$, $Al_2O_3$, $K_2O$, CaO, and ZnO.

5. The method of claim 3, wherein the liquid sample is blood, plasma, serum, urine, or a lysate thereof.

6. The method of claim 3, wherein the liquid sample has a volume of at least 2 ml.

7. The method of claim 6, wherein the liquid sample has a volume of 2 ml to 100 ml.

8. The method of claim 6, wherein the vessel holds a volume of 2 ml or less.

9. The method of claim 6, wherein the vessel holds a volume of 0.5 ml to 2 ml.

10. The method of claim 6, further comprising eluting and separating the nucleic acids from the MGPs.

11. The method of claim 6, wherein the method is automated.

12. The method of claim 6, wherein step (e) comprises pipetting the MGPs in the liquid sample.

13. The method of claim 6, wherein the nucleic acids are RNA.

14. The method of claim 6, wherein the nucleic acids are DNA.

15. The method of claim 6, wherein the vessel is a well in a multi-well plate or a tube.

16. The method of claim 6, wherein step (c) comprises removing unbound liquid sample from the MGPs, washing the MGPs, and removing unbound material from the MGPs.

17. The method of claim 6, wherein step (h) comprises removing unbound liquid sample from the MGPs, washing the MGPs, and removing unbound material from the MGPs.

\* \* \* \* \*